United States Patent
Hahn et al.

(10) Patent No.: US 9,593,377 B2
(45) Date of Patent: Mar. 14, 2017

(54) SIGNATURES AND DETERMINANTS ASSOCIATED WITH CANCER AND METHODS OF USE THEREOF

(75) Inventors: William C. Hahn, Newton, MA (US); Pablo Tamayo, Hopkinton, MA (US); Jesse S. Boehm, Jamaica Plain, MA (US); Jill P. Mesirov, Belmont, MA (US)

(73) Assignees: Dana-Farber Cancer Institute, Inc., Boston, MA (US); The Broad Institute, Inc., Cambridge, MA (US)

( * ) Notice: Subject to any disclaimer, the term of this patent is extended or adjusted under 35 U.S.C. 154(b) by 402 days.

(21) Appl. No.: 13/990,710

(22) PCT Filed: Nov. 30, 2011

(86) PCT No.: PCT/US2011/062516
§ 371 (c)(1),
(2), (4) Date: Aug. 19, 2013

(87) PCT Pub. No.: WO2012/075069
PCT Pub. Date: Jun. 7, 2012

(65) Prior Publication Data
US 2013/0323744 A1   Dec. 5, 2013

Related U.S. Application Data

(60) Provisional application No. 61/419,101, filed on Dec. 2, 2010.

(51) Int. Cl.
| | |
|---|---|
| *C12Q 1/68* | (2006.01) |
| *G06F 19/20* | (2011.01) |
| *G06F 19/18* | (2011.01) |
| *G06F 19/24* | (2011.01) |

(52) U.S. Cl.
CPC ......... *C12Q 1/6886* (2013.01); *G06F 19/20* (2013.01); *C12Q 2600/106* (2013.01); *C12Q 2600/136* (2013.01); *C12Q 2600/158* (2013.01); *G06F 19/18* (2013.01); *G06F 19/24* (2013.01)

(58) Field of Classification Search
None
See application file for complete search history.

(56) References Cited

U.S. PATENT DOCUMENTS

| | | |
|---|---|---|
| 2004/0121343 A1 | 6/2004 | Buechler et al. |
| 2006/0210979 A1* | 9/2006 | Yang .................... C12Q 1/6818 435/6.14 |
| 2007/0212702 A1 | 9/2007 | Tomlins et al. |
| 2009/0215053 A1 | 8/2009 | Galon et al. |
| 2010/0075323 A1 | 3/2010 | Terng et al. |
| 2010/0279301 A1 | 11/2010 | Chinnaiyan et al. |
| 2011/0081362 A1* | 4/2011 | Elledge ................ C12N 15/111 424/174.1 |

FOREIGN PATENT DOCUMENTS

JP   2005-304497   11/2005

* cited by examiner

*Primary Examiner* — David Thomas
(74) *Attorney, Agent, or Firm* — Cooley LLP; Ivor Elrifi; Cynthia A. Kozakiewicz

(57) ABSTRACT

The present invention provides methods of detecting cancer using biomarkers.

5 Claims, 2 Drawing Sheets

SIGNATURES AND DETERMINANTS ASSOCIATED WITH CANCER AND METHODS OF USE THEREOF

REFERENCE TO RELATED APPLICATIONS

This application is a national stage application, filed under 35 U.S.C. §371, of PCT Application No. PCT/US2011/062516, filed Nov. 30, 2011, which claims the benefit of provisional application U.S. Ser. No. 61/419,101, filed Dec. 2, 2010, the contents of which are herein incorporated by reference in its entirety.

GOVERNMENT SUPPORT CLAUSE

This invention was made with government support under grant number U54 CA112962 awarded by The National Institutes of Health. The government has certain rights in the invention.

FIELD OF THE INVENTION

The present invention relates generally to the identification of biological signatures associated with KRAS activation in human cells and methods of using such biological signatures in the screening, prevention, diagnosis, therapy, monitoring, and prognosis of cancer.

BACKGROUND OF THE INVENTION

One of the goals of modern cancer research is to decompose the oncogenic state of individual tumors directly in terms of cellular pathways that are aberrantly activated or deregulated. Despite large-scale efforts to systematically map the cancer genome, determining how alterations present within a given tumor interact to induce activated cellular states represents a major unmet challenge. The use of expression-based signatures has been effective in terms of improving classification of tumor samples according to sub-types, prognostic groups, or drug response. However, several significant limitations and challenges remain in order to make signature-based characterization effective and systematic enough to profile large and diverse collections of individual human tumors. For oncogenic signatures these limitations specifically include, but are not limited to, i) the uneven quality of experimental signatures from the literature, ii) the lack of validation in independent datasets, iii) the lack of transparency and annotation of the signatures, iv) the lack of specificity with respect to the genetic lesion they represent, and v) the limited understanding of their universality, tissue specificity and relevance to an in vivo context.

Thus a need exists for the identification of expression based signatures that are capable of classifying tumors.

SUMMARY OF THE INVENTION

In one aspect, the invention provides methods with a predetermined level of predictability for determining the presence of a tumor in a subject by analyzing a subject sample to obtain a subject gene expression profile and comparing the subject gene expression profile to a KRAS activation profile. A similarity of the subject gene expression profile and the KRAS activation profile indicates the presence of a tumor in the subject.

In another aspect the invention provides a method with a predetermined level of predictability for assessing a risk of development of a tumor in a subject by analyzing a subject sample to obtain a subject gene expression profile and comparing the subject gene expression profile to a KRAS activation profile. A similarity of the subject gene expression profile and the KRAS activation profile indicates a risk of development of a tumor in the subject.

Optionally, the methods include further measuring at least one standard parameters associated with the tumor.

In a further aspect, the invention provides a method with a predetermined level of predictability for assessing the progression of a tumor in a subject by analyzing a first sample from the subject at a first period of time obtain a first gene expression profile; analyzing a second sample from the subject at a second period of time obtain a second gene expression profile and comparing the first and second gene expression profile. The first sample is taken from the subject prior to being treated for the tumor and the second sample is taken from the subject after being treated for the tumor.

In yet another aspect, the invention provides a method with a predetermined level of predictability for monitoring the effectiveness of treatment for a tumor by analyzing in a first sample from the subject at a first period of time to obtain a first gene expression profile; analyzing in a second sample from the subject at a second period of time to obtain a second gene expression profile and comparing the first and second gene expression profile wherein the effectiveness of treatment is monitored by an alteration between the first and second gene expression profile. The subject has previously been treated for the tumor. The first sample is taken from the subject prior to being treated for the tumor and the second sample is taken from the subject after being treated for the tumor.

Also provide by the invention is a KRAS activation expression profile having a pattern of marker levels of an effective amount of two or more markers selected from DETERMINANTS 1-600. In some aspects the gene expression profile is contained on machine readable media and optionally, additional test results and subject information are included on the media The invention also provides a kit comprising a plurality of DETERMINANT detection reagents that detect the corresponding DETERMINANTS selected from DETERMINANTS 1-600.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

Figure 1:
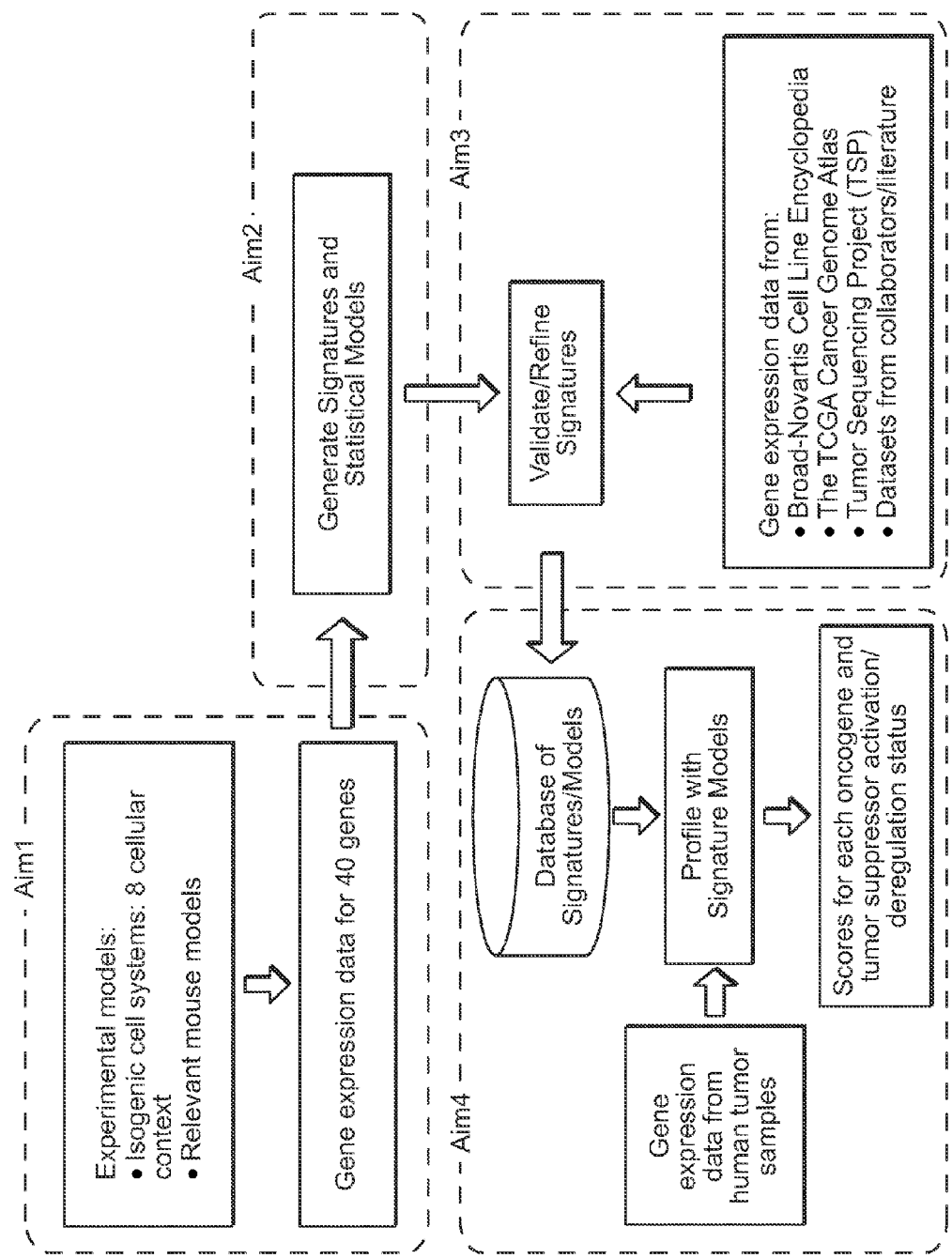
FIG. 1 is an illustration showing the basic methodology for creation of signatures from experimental models, training of statistical models, validation and refinement of signatures and database creation.

The present invention relates to the identification of signatures and determinants associated with subjects with a tumor or are at risk for developing a tumor. Specifically, the invention provides an expression signature that represents activation of the KRAS oncogene. The KRAS signature is not present in normal tissue. Accordingly the KRAS activation signature disclosed herein is useful for the characterization of tumors from individual patients to assess their KRAS activation status; stratify patients for prognosis and risk assessment; and to match tumors to effective inhibitor drugs or treatments that target the KRAS oncogene or the RAS pathway.

Ras proteins are small regulatory GTP-binding proteins, or small G proteins, which belong to the Ras protein superfamily. They are monomeric GTPases, but their GTPase activity is very slow (less than one GTP molecule per minute). Ras proteins are key relays in the signal-transducing cascade induced by the binding of a ligand to specific receptors such as receptor tyrosine kinases (RTKs), since they trigger the MAP kinase cascade. The ligand can be a growth factor (epidermal growth factor (EGF), platelet-derived growth factor (PDGF), insulin, an interleukin (IL), granulocyte colony-stimulating factor (G-CSF), granulocyte/macrophage colony-stimulating factor (GM-CSF). Ras proteins contain sequences highly conserved during evolution. Their tertiary structure includes ten loops connecting six strands of beta-sheet and five alpha helices.

In mammalians, there are four Ras proteins, which are encoded by Ha-ras, N-ras, Ki-rasA and Ki-rasB genes. They are composed of about 170 residues and have a relative molecular mass of 21 kD. Ras proteins contain covalently attached modified lipids allowing these proteins to bind to the plasma membrane. Ha-Ras has a C-terminal farnesyl group, a C-terminal palmitoyl group and a N-terminal myristoyl group. In Ki-Ras(B), a C-terminal polylysine domain replaces the palmitoyl group.

Functionally, a RAS protein alternates between two forms in the cell. When unattached to the cell membrane and bound to the compound GDP (guanine diphosphate), the RAS protein is in its biologically inactive state. For RAS to become active, several events must occur. First, the protein must be chemically modified by a process called farnesylation. This modification attaches a fatty acid side chain onto the RAS protein, enhancing its ability to associate with the lipid-rich inner cell membrane. Once anchored to the cell membrane, RAS can then interact with several other proteins to complete its activation. These include membrane-spanning protein receptors that bind informational molecules that are presented on the outside of the cell membrane, and a variety of accessory molecules that mediate the interaction between RAS and the receptor protein. These latter molecules, so-called exchange and adapter proteins, also assist in the release of GDP from the RAS protein and the binding of GTP (guanine triphosphate), which is the final step in activation.

Activation of the wild-type RAS proteins is a reversible process. RAS itself is also a GTPase, that is, it hydrolyzes GTP to form GDP. The rate of this conversion, which is greatly enhanced by other cellular proteins known as GTPase-activating proteins (GAPs), is the key factor that determines how long the RAS-mediated signal persists in the cell. Once activated, RAS triggers a cascade of signals that are conveyed from the cell membrane into the nucleus of the cell. These signals are mediated by a series of kinases, enzymes that catalyze the phosphorylation of cellular proteins. Ultimately, this pathway results in the activation of nuclear proteins called transcription factors, which act to increase the rate of transcription of specific genes within the cell. When activated, KRAS can signal into the cytosol via multiple downstream signaling pathways such as the classical MAPK pathway, the phosphatidylinositol ("PI3") kinase pathway, and the JNK pathway, to induce a plethora of cellular changes, including enhanced proliferation and cell survival Many of the genes whose transcription are upregulated by RAS activation are involved in the control of cell cycling, and thus persistent activation of RAS, which can be caused by mutations in the ras gene which impair the protein's GTPase activity, can lead to abnormalities in cellular proliferation. In fact, this mechanism has been implicated in the development of a wide variety of human cancers. Members of the Ras oncogene family transform most immortalized cell lines in vitro, and mutations of Ras genes occur in about 30% of cancer-related human tumors In addition, activation of the Ras pathway is frequent in human tumors even in the absence of Ras mutations.

The invention provides a KRAS signature that is represents KRAS activation regardless of the presence of a mutation; accordingly, the present invention provides a superior method of detecting tumors than mutational analysis.

Accordingly, the invention provides methods for identifying subjects who have a tumor, or who at risk for experiencing a tumor by the detection of determinants associated with KRAS signature, including those subjects who are asymptomatic for the tumor. The KRAS signatures and determinants are also useful for monitoring subjects undergoing treatments and therapies for cancer, and for selecting or modifying therapies and treatments that would be efficacious in subjects having cancer, wherein selection and use of such treatments and therapies slow the progression of the tumor, or substantially delay or prevent its onset, or reduce or prevent the incidence of tumor metastasis.

DEFINITIONS

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"Determinant" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Determinants can also include mutated proteins or mutated nucleic acids. Determinants also encompass non-blood borne factors or non-analyte physiological markers of health status, such as "clinical parameters" defined herein, as well as "traditional laboratory risk factors", also defined herein. Determinants also include any calculated indices created mathematically or combinations of any one or more of the foregoing measurements, including temporal trends and differences. Where available, and unless otherwise described herein, determinants which are gene products are identified based on the official letter abbreviation or gene symbol assigned by the international Human Genome Organization Naming Committee (HGNC) and listed at the date of this filing at the US National Center for Biotechnology Information (NCBI) web site (http://www.ncbi.nlm.nih.gov/sites/entrez?db=gene), also known as Entrez Gene.

"DETERMINANT" OR "DETERMINANTS" encompass one or more of all nucleic acids or polypeptides whose levels are changed in subjects in which KRAS is activated. Individual DETERMINANTS are summarized in Table 1 and Table 2 and are collectively referred to herein as, inter alia, "KRAS activation-associated proteins", "DETERMINANT polypeptides", or "DETERMINANT proteins". The corresponding nucleic acids encoding the polypeptides are referred to as "KRAS activation-associated nucleic acids", "KRAS activation-associated genes", "DETERMINANT nucleic acids", or "DETERMINANT genes". Unless indicated otherwise, "DETERMINANT", "KRAS activation-associated proteins", "KRAS activation-associated nucleic acids" are meant to refer to any of the sequences disclosed herein. The corresponding metabolites of the DETERMINANT proteins or nucleic acids can also be measured, as well as any of the aforementioned traditional risk marker metabolites.

Physiological markers of health status (e.g., such as age, family history, and other measurements commonly used as traditional risk factors) are referred to as "DETERMINANT physiology". Calculated indices created from mathematically combining measurements of one or more, preferably two or more of the aforementioned classes of DETERMINANTS are referred to as "DETERMINANT indices".

"Clinical parameters" encompasses all non-sample or non-analyte biomarkers of subject health status or other characteristics, such as, without limitation, age (Age), ethnicity (RACE), gender (Sex), or family history (FamHX).

"Circulating endothelial cell" ("CEC") is an endothelial cell from the inner wall of blood vessels, which sheds into the bloodstream under certain circumstances, including inflammation, and contributes to the formation of new vasculature associated with cancer pathogenesis. CECs may be useful as a marker of tumor progression and/or response to antiangiogenic therapy.

"Circulating tumor cell" ("CTC") is a tumor cell of epithelial origin, which is shed from the primary tumor upon metastasis, and enters the circulation. The number of circulating tumor cells in peripheral blood is associated with prognosis in patients with metastatic cancer. These cells can be separated and quantified using immunologic methods that detect epithelial cells.

"FN" is false negative, which for a disease state test means classifying a disease subject incorrectly as non-disease or normal.

"FP" is false positive, which for a disease state test means classifying a normal subject incorrectly as having disease.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use in combining DETERMINANTS and other determinant are linear and non-linear equations and statistical classification analyses to determine the relationship between levels of DETERMINANTS detected in a subject sample and the subject's risk of metastatic disease. In panel and combination construction, of particular interest are structural and syntactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, among others. Other techniques may be used in survival and time to event hazard analysis, including Cox, Weibull, Kaplan-Meier and Greenwood models well known to those of skill in the art. Many of these techniques are useful either combined with a DETERMINANT selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Measuring" or "measurement," or alternatively "detecting" or "detection," means assessing the presence, absence, quantity, activity or amount (which can be an effective amount) of either a given substance within a clinical or subject-derived sample, including the derivation of qualitative or quantitative concentration levels of such substances, or otherwise evaluating the values or categorization of a subject's non-analyte clinical parameters.

"Negative predictive value" or "NPV" is calculated by TN/(TN+FN) or the true negative fraction of all negative test results. It also is inherently impacted by the prevalence of the disease and pre-test probability of the population intended to be tested.

See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

Finally, hazard ratios and absolute and relative risk ratios within subject cohorts defined by a test are a further measurement of clinical accuracy and utility. Multiple methods are frequently used to defining abnormal or disease values, including reference limits, discrimination limits, and risk thresholds.

"Analytical accuracy" refers to the reproducibility and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, and other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC, time to result, shelf life, etc. as relevant.

"Positive predictive value" or "PPV" is calculated by TP/(TP+FP) or the true positive fraction of all positive test results. It is inherently impacted by the prevalence of the disease and pre-test probability of the population intended to be tested.

"Risk" in the context of the present invention, relates to the probability that an event will occur over a specific time period, as in the conversion to metastatic events, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion.

"Risk evaluation," or "evaluation of risk" in the context of the present invention encompasses making a prediction of the probability, odds, or likelihood that an event or disease state may occur, the rate of occurrence of the event or conversion from one disease state to another, i.e., from a primary tumor to a metastatic tumor or to one at risk of developing a metastatic, or from at risk of a primary metastatic event to a more secondary metastatic event. Risk evaluation can also comprise prediction of future clinical parameters, traditional laboratory risk factor values, or other indices of cancer, either in absolute or relative terms in reference to a previously measured population. The methods of the present invention may be used to make continuous or categorical measurements of the risk of a metastatic tumor thus diagnosing and defining the risk spectrum of a category of subjects defined as being at risk for metastatic tumor. In the categorical scenario, the invention can be used to discriminate between normal and other subject cohorts at higher risk for metastatic tumors. Such differing use may require different DETERMINANT combinations and individualized panels, mathematical algorithms, and/or cut-off points, but be subject to the same aforementioned measurements of accuracy and performance for the respective intended use.

A "sample" in the context of the present invention is a biological sample isolated from a subject and can include, by way of example and not limitation, tissue biopsies, whole blood, serum, plasma, blood cells, endothelial cells, lymphatic fluid, ascites fluid, interstitial fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, circulating tumor cell, circulating endothelial cell or any other secretion, excretion, or other bodily fluids.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of tumor metastasis. A subject can be male or female. A subject can be one who has been previously diagnosed or identified as having primary tumor or a metastatic tumor, and optionally has already undergone, or is undergoing, a therapeutic intervention for the tumor. Alternatively, a subject can also be one who has not been previously diagnosed as having a metastatic tumor. For example, a subject can be one who exhibits one or more risk factors for a metastatic tumor.

"TN" is true negative, which for a disease state test means classifying a non-disease or normal subject correctly.

"TP" is true positive, which for a disease state test means correctly classifying a disease subject.

"Traditional laboratory risk factors" correspond to biomarkers isolated or derived from subject samples and which are currently evaluated in the clinical laboratory and used in traditional global risk assessment algorithms. Traditional laboratory risk factors for tumor metastasis include for example breslow thickness, ulceration. Proliferative index, tumor-infiltrating lymphocytes. Other traditional laboratory risk factors for tumor metastasis are known to those skilled in the art.

Methods and Uses of the Invention

The methods disclosed herein are used with subjects at risk for developing a tumor, subjects who may or may not have already been diagnosed with a tumor and subjects undergoing treatment and/or therapies for a primary tumor or a metastatic tumor. The methods of the present invention can also be used to monitor or select a treatment regimen for a subject who has a primary tumor or a metastatic tumor, and to screen subjects who have not been previously diagnosed as having a tumor, such as subjects who exhibit risk factors for cancer. Preferably, the methods of the present invention are used to identify and/or diagnose subjects who are asymptomatic for a tumor. "Asymptomatic" means not exhibiting the traditional symptoms.

The methods of the present invention may also used to identify and/or diagnose subjects already at higher risk of developing a tumor based on solely on the traditional risk factors.

A subject having a tumor can be identified by detecting the KRAS SIGNATURE described herein. Additionally, a subject having a tumor can be identified by measuring the amounts (including the presence or absence) of an effective number (which can be two or more) of DETERMINANTS in a subject-derived sample and the amounts are then compared to a reference value. Alterations in the amounts and patterns of expression of biomarkers, such as proteins, polypeptides, nucleic acids and polynucleotides, polymorphisms of proteins, polypeptides, nucleic acids, and polynucleotides, mutated proteins, polypeptides, nucleic acids, and polynucleotides, or alterations in the molecular quantities of metabolites or other analytes in the subject sample compared to the reference value are then identified.

A reference value can be relative to a number or value derived from population studies, including without limitation, such subjects having the same cancer, subject having the same or similar age range, subjects in the same or similar ethnic group, subjects having family histories of cancer, or relative to the starting sample of a subject undergoing treatment for a cancer. Such reference values can be derived from statistical analyses and/or risk prediction data of populations obtained from mathematical algorithms and computed indices of cancer metastasis. Reference SIGNATURE and/or DETERMINANT indices can also be constructed and used using algorithms and other methods of statistical and structural classification.

In one embodiment of the present invention, the reference value is the amount of DETERMINANTS in a control sample derived from one or more subjects who are not at risk or at low risk for developing tumor. In another embodiment of the present invention, the reference value is the amount of DETERMINANTS in a control sample derived from one or more subjects who are asymptomatic and/or lack traditional risk factors for a tumor. In a further embodiment, such subjects are monitored and/or periodically retested for a diagnostically relevant period of time ("longitudinal studies") following such test to verify continued absence of a tumor (disease or event free survival). Such period of time may be one year, two years, two to five years, five years, five to ten years, ten years, or ten or more years from the initial testing date for determination of the reference value. Furthermore, retrospective measurement of DETERMINANTS in properly banked historical subject samples may be used in establishing these reference values, thus shortening the study time required.

A reference value can also comprise the amounts of DETERMINANTS derived from subjects who show an improvement in risk factors as a result of treatments and/or therapies for the cancer. A reference value can also comprise the amounts of DETERMINANTS derived from subjects who have confirmed disease by known invasive or non-invasive techniques, or are at high risk for developing a tumor, or who have suffered from a tumor.

In another embodiment, the reference value is an index value or a baseline value. An index value or baseline value is a composite sample of an effective amount of DETERMINANTS from one or more subjects who do not have a tumor or subjects who are asymptomatic a tumor. A baseline value can also comprise the amounts of DETERMINANTS in a sample derived from a subject who has shown an improvement in tumor risk factors as a result of cancer treatments or therapies. In this embodiment, to make comparisons to the subject-derived sample, the amounts of DETERMINANTS are similarly calculated and compared to the index value. Optionally, subjects identified as having metastasis tumor, or being at increased risk of developing a tumor are chosen to receive a therapeutic regimen to slow the progression the cancer, or decrease or prevent the risk of developing a tumor or metastasis.

The progression of a tumor, or effectiveness of a cancer treatment regimen can be monitored by detecting the SIGNATURE or a DETERMINANT in an effective amount (which may be two or more) of samples obtained from a subject over time and comparing the SIGNATURE or the amount of DETERMINANTS detected. For example, a first sample can be obtained prior to the subject receiving treatment and one or more subsequent samples are taken after or during treatment of the subject. The cancer is considered to be progressive (or, alternatively, the treatment does not prevent progression) if the SIGNATURE or the amount of DETERMINANT changes over time relative to the reference value, whereas the cancer is not progressive if the SIGNATURE or the amount of DETERMINANTS remains constant over time (relative to the reference population, or "constant" as used herein). The term "constant" as used in the context of the present invention is construed to include changes over time with respect to the reference value.

Additionally, therapeutic or prophylactic agents suitable for administration to a particular subject can be identified by detecting the SIGNATURE OR a DETERMINANT in an effective amount (which may be two or more) in a sample obtained from a subject, exposing the subject-derived sample to a test compound and determining the SIGNATURE or the amount (which may be two or more) of DETERMINANTS in the subject-derived sample. Accordingly, treatments or therapeutic regimens for use in subjects having a cancer, or subjects at risk for developing a tumor can be selected based on the SIGNATURE or the amounts of DETERMINANTS in samples obtained from the subjects and compared to a reference value. Two or more treatments or therapeutic regimens can be evaluated in parallel to determine which treatment or therapeutic regimen would be the most efficacious for use in a subject to delay onset, or slow progression of the cancer.

The present invention further provides a method for screening for changes in marker expression associated with the KRAS SIGNATURE, by determining the amount (which may be two or more) of DETERMINANTS in a subject-derived sample, comparing the amounts of the DETERMINANTS in a reference sample, and identifying alterations in amounts in the subject sample compared to the reference sample.

The present invention further provides a method of treating a patient with a tumor, by identifying a patient with a tumor where the KRAS signature is present and/or an effective amount of DETERMINANTS are altered in a clinically significant manner as measured in a sample from the tumor, and treating the patient with a therapeutic regimen that prevents or reduces the tumor and/or tumor metastasis.

Information regarding a treatment decision for a tumor patient by obtaining information on the KRAS SIGNATURE and/or an effective amount of DETERMINANTS in a tumor sample from the patient, and selecting a treatment regimen that prevents or reduces tumor progression in the patient if the SIGNATURE or two or more DETERMINANTS are altered in a clinically significant manner.

By "efficacious", it is meant that the treatment leads to an alteration in the amount or activity of a DETERMINANT protein, nucleic acid, polymorphism, metabolite, or other analyte or the absence of the KRAS signature. Assessment of the risk factors disclosed herein can be achieved using standard clinical protocols. Efficacy can be determined in association with any known method for diagnosing, identifying, or treating a metastatic disease.

The present invention also provides DETERMINANT panels including one or more DETERMINANTS that are indicative of a general physiological pathway associated with the cancer. For example, one or more DETERMINANTS that can be used to exclude or distinguish between different disease states or sequelae associated with metastasis. A single DETERMINANT may have several of the aforementioned characteristics according to the present invention, and may alternatively be used in replacement of one or more other DETERMINANTS where appropriate for the given application of the invention.

The present invention also comprises a kit with a detection reagent that binds to two or more DETERMINANT proteins, nucleic acids, polymorphisms, metabolites, or other analytes. Also provided by the invention is an array of detection reagents, e.g., antibodies and/or oligonucleotides that can bind to two or more DETERMINANT proteins or nucleic acids, respectively. In one embodiment, the DETERMINANT are proteins and the array contains antibodies that bind an effective amount of DETERMINANTS sufficient to measure a statistically significant alteration in DETERMINANT expression compared to a reference value. In another embodiment, the DETERMINANTS are nucleic acids and the array contains oligonucleotides or aptamers that bind an effective amount of DETERMINANTS sufficient to measure a statistically significant alteration in DETERMINANT expression compared to a reference value.

Also provided by the present invention is a method for treating one or more subjects at risk for developing a tumor by detecting the presence the SIGNATURE or altered amounts of an effective amount of DETERMINANTS present in a sample from the one or more subjects; and treating the one or more subjects with one or more cancer-modulating drugs until altered amounts or activity of the SIGNATURE or DETERMINANTS return to a baseline value measured in one or more subjects at low risk for developing a metastatic disease, or alternatively, in subjects who do not exhibit any of the traditional risk factors for metastatic disease.

Diagnostic and Prognostic Indications of the Invention

The invention allows the diagnosis and prognosis of a tumor. The risk of developing a tumor can be detected by measuring the KRAS SIGNATURE or an effective amount of DETERMINANT proteins, nucleic acids, polymorphisms, metabolites, and other analytes (which may be two or more) in a test sample (e.g., a subject derived sample), and comparing the effective amounts to reference or index values, often utilizing mathematical algorithms or formula in order to combine information from results of multiple individual DETERMINANTS and from non-analyte clinical parameters into a single measurement or index. Subjects identified as having an increased risk of a tumor can optionally be selected to receive treatment regimens, such as administration of prophylactic or therapeutic compounds to prevent or delay the onset of a metastatic tumor.

The amount of the DETERMINANT protein, nucleic acid, polymorphism, metabolite, or other analyte can be measured in a test sample and compared to the "normal control level," utilizing techniques such as reference limits, discrimination limits, or risk defining thresholds to define cutoff points and abnormal values. The "normal control level" means the level of one or more DETERMINANTS or combined DETERMINANT indices typically found in a subject not suffering from a metastatic tumor. Such normal control level and cutoff points may vary based on whether a DETERMINANT is used alone or in a formula combining with other DETERMINANTS into an index. Alternatively, the normal control level can be a database of DETERMINANT patterns from previously tested subjects who did not develop a tumor over a clinically relevant time horizon.

The present invention may be used to make continuous or categorical measurements of the risk of conversion to a tumor, thus diagnosing and defining the risk spectrum of a category of subjects defined as at risk for having a cancerous event. In the categorical scenario, the methods of the present invention can be used to discriminate between normal and disease subject cohorts. In other embodiments, the present invention may be used so as to discriminate those at risk for having a metastatic event from those having more rapidly progressing (or alternatively those with a shorter probable time horizon to a metastatic event) to a metastatic event from those more slowly progressing (or with a longer time horizon to a metastatic event), or those having a metastatic tumor from normal. Such differing use may require different DETERMINANT combinations in individual panel, mathematical algorithm, and/or cut-off points, but be subject to the same aforementioned measurements of accuracy and other performance metrics relevant for the intended use.

Identifying the subject at risk of having a cancerous vent enables the selection and initiation of various therapeutic interventions or treatment regimens in order to delay, reduce or prevent that subject's conversion to a disease state. The SIGNATURE or levels of an effective amount of DETERMINANT proteins, nucleic acids, polymorphisms, metabolites, or other analytes also allows for the course of treatment of a tumor to be monitored. In this method, a biological sample can be provided from a subject undergoing treatment regimens, e.g., drug treatments, for cancer. If desired, biological samples are obtained from the subject at various time points before, during, or after treatment.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like cancer or metastatic events, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018, 067. Such systems can access the data directly from internal data storage or remotely from one or more data storage sites as further detailed herein.

A machine-readable storage medium can comprise a data storage material encoded with machine readable data or data arrays which, when using a machine programmed with instructions for using said data, is capable of use for a variety of purposes, such as, without limitation, subject information relating to metastatic disease risk factors over time or in response drug therapies. Measurements of effective amounts of the biomarkers of the invention and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein.

The SIGNATURE or levels of an effective amount of DETERMINANT proteins, nucleic acids, polymorphisms, metabolites, or other analytes can then be determined and compared to a reference value, e.g. a control subject or population whose metastatic state is known or an index value or baseline value. The reference sample or index value or baseline value may be taken or derived from one or more subjects who have been exposed to the treatment, or may be taken or derived from one or more subjects who are at low risk of developing cancer or a metastatic event, or may be taken or derived from subjects who have shown improvements in as a result of exposure to treatment. Alternatively, the reference sample or index value or baseline value may be taken or derived from one or more subjects who have not been exposed to the treatment. For example, samples may be collected from subjects who have received initial treatment for cancer or a metastatic event and subsequent treatment for cancer or a metastatic event to monitor the progress of the treatment. A reference value can also comprise a value derived from risk prediction algorithms or computed indices from population studies such as those disclosed herein.

The DETERMINANTS of the present invention can thus be used to generate a "reference DETERMINANT profile" of those subjects who do not have cancer or are not at risk of having a metastatic event, and would not be expected to develop cancer or a metastatic event. The DETERMINANTS disclosed herein can also be used to generate a "subject DETERMINANT profile" taken from subjects who have cancer or are at risk for having a metastatic event. The subject DETERMINANT profiles can be compared to a reference DETERMINANT profile to diagnose or identify subjects at risk for developing cancer or a metastatic event, to monitor the progression of disease, as well as the rate of progression of disease, and to monitor the effectiveness of treatment modalities. The reference and subject DETERMINANT profiles and or SIGNATURE of the present invention can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

Differences in the genetic makeup of subjects can result in differences in their relative abilities to metabolize various drugs, which may modulate the symptoms or risk factors of cancer or metastatic events. Subjects that have cancer, or at risk for developing cancer or a metastatic event can vary in age, ethnicity, and other parameters. Accordingly, use of the SIGNATURE and DETERMINANTS disclosed herein, both alone and together in combination with known genetic factors for drug metabolism, allow for a pre-determined level of predictability that a putative therapeutic or prophylactic to be tested in a selected subject will be suitable for treating or preventing cancer or a metastatic event in the subject.

To identify therapeutics or drugs that are appropriate for a specific subject, a test sample from the subject can also be exposed to a therapeutic agent or a drug, and the SIGNATURE and/or the level of one or more of DETERMINANT proteins, nucleic acids, polymorphisms, metabolites or other analytes can be determined. The SIGNATURE and/or level of one or more DETERMINANTS can be compared to sample derived from the subject before and after treatment or exposure to a therapeutic agent or a drug, or can be compared to samples derived from one or more subjects who have shown improvements in risk factors (e.g., clinical parameters or traditional laboratory risk factors) as a result of such treatment or exposure.

A subject cell (i.e., a cell isolated from a subject) can be incubated in the presence of a candidate agent and SIGNATURE or the pattern of DETERMINANT expression in the test sample is measured and compared to a reference profile, e.g., a metastatic disease reference expression profile or a non-disease reference expression profile or an index value or baseline value. The test agent can be any compound or composition or combination thereof, including, dietary supplements. For example, the test agents are agents frequently used in cancer treatment regimens and are described herein.

The aforementioned methods of the invention can be used to evaluate or monitor the progression and/or improvement of subjects who have been diagnosed with a cancer, and who have undergone surgical interventions.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic or prognostic test, assay, or method concerns the ability of the test, assay, or method to distinguish between subjects having cancer, or at risk for cancer or a metastatic event, is based on whether the subjects have, a "significant alteration" (e.g., clinically significant "diagnostically significant) in the levels of a DETERMINANT. By "effective amount" it is meant that the measurement of an appropriate number of DETERMINANTS (which may be one or more) to produce a "significant alteration," (e.g. level of expression or activity of a DETERMINANT) that is different than the predetermined cut-off point (or threshold value) for that DETERMINANT(S) and therefore indicates that the subject has cancer or is at risk for having a metastatic event for which the DETERMINANT(S) is a determinant. The difference in the level of DETERMINANT between normal and abnormal is preferably statistically significant. As noted below, and without any limitation of the invention, achieving statistical significance, and thus the preferred analytical, diagnostic, and clinical accuracy, generally but not always requires that combinations of several DETERMINANTS be used together in panels and combined with mathematical algorithms in order to achieve a statistically significant DETERMINANT index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

By predetermined level of predictability it is meant that the method provides an acceptable level of clinical or diagnostic accuracy. Using such statistics, an "acceptable degree of diagnostic accuracy", is herein defined as a test or assay (such as the test of the invention for determining the clinically significant presence of DETERMINANTS, which thereby indicates the presence of cancer and/or a risk of having a metastatic event) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of a cancer, metastatic cancer or response to therapy with at least 75% accuracy, more preferably 80%, 85%, 90%, 95%, 97%, 98%, 99% or greater accuracy.

The predictive value of any test depends on the sensitivity and specificity of the test, and on the prevalence of the condition in the population being tested. This notion, based on Bayes' theorem, provides that the greater the likelihood that the condition being screened for is present in an individual or in the population (pre-test probability), the greater the validity of a positive test and the greater the likelihood that the result is a true positive. Thus, the problem with using a test in any population where there is a low likelihood of the condition being present is that a positive result has limited value (i.e., more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for developing cancer or metastatic event, and the bottom quartile comprising the group of subjects having the lowest relative risk for developing cancer or a metastatic event. Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy."Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future metastatic events. Often such lower diagnostic accuracy tests must be combined with additional parameters in order to derive meaningful clinical thresholds for therapeutic intervention, as is done with the aforementioned global risk assessment indices.

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category (such as those at risk for having a metastatic event) has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective amount of the DETERMINANTS of the invention allows for one of skill in the art to use the DETERMINANTS to identify, diagnose, or prognose subjects with a pre-determined level of predictability and performance.

Risk Markers of the Invention (DETERMINANTS)

The biomarkers and methods of the present invention allow one of skill in the art to identify, diagnose, or otherwise assess those subjects who do not exhibit any symptoms of cancer or a metastatic event, but who nonetheless may be at risk for developing cancer or a metastatic event.

Table I comprises the three hundred (300) overexpressed/amplified or downregulated/deleted DETERMINANTS making up the KRAS SIGNATURE of the present invention One skilled in the art will recognize that the DETERMINANTS presented herein encompasses all forms and variants, including but not limited to, polymorphisms, isoforms, mutants, derivatives, precursors including nucleic acids and pro-proteins, cleavage products, receptors (including soluble and transmembrane receptors), ligands, protein-ligand complexes, and post-translationally modified variants (such as cross-linking or glycosylation), fragments, and degradation products, as well as any multi-unit nucleic acid, protein, and glycoprotein structures comprised of any of the DETERMINANTS as constituent sub-units of the fully assembled structure.

One skilled in the art will note that the above listed DETERMINANTS come from a diverse set of physiological and biological pathways, including many which are not commonly accepted to be related to metastatic disease. These groupings of different DETERMINANTS, even within those high significance segments, may presage differing signals of the stage or rate of the progression of the disease. Such distinct groupings of DETERMINANTS may allow a more biologically detailed and clinically useful signal from the DETERMINANTS as well as opportunities for pattern recognition within the DETERMINANT algorithms combining the multiple DETERMINANT signals.

The present invention concerns, in one aspect, a subset of DETERMINANTS; other DETERMINANTS and even biomarkers which are not listed in Table 1 and Table 2, but related to these physiological and biological pathways, may prove to be useful given the signal and information provided from these studies. To the extent that other biomarker pathway participants (i.e., other biomarker participants in common pathways with those biomarkers contained within the list of DETERMINANTS in Table 1 and Table 2) are also relevant pathway participants in cancer. These other pathway participants are also considered DETERMINANTS in the context of the present invention, provided they additionally share certain defined characteristics of a good biomarker, which would include both involvement in the herein disclosed biological processes and also analytically important characteristics such as the bioavailability of said biomarkers at a useful signal to noise ratio, and in a useful and accessible sample matrix such as blood serum. Such requirements typically limit the diagnostic usefulness of many members of a biological pathway, and frequently occurs only in pathway members that constitute secretory substances, those accessible on the plasma membranes of cells, as well as those that are released into the serum upon cell death, due to apoptosis or for other reasons such as endothelial remodeling or other cell turnover or cell necrotic processes, whether or not they are related to the disease progression of cancer or metastatic event. However, the remaining and future biomarkers that meet this high standard for DETERMINANTS are likely to be quite valuable.

Furthermore, other unlisted biomarkers will be very highly correlated with the biomarkers listed as DETERMINANTS in Table 1 and Table 2 (for the purpose of this application, any two variables will be considered to be "very highly correlated" when they have a Coefficient of Determination ($R^2$) of 0.5 or greater). The present invention encompasses such functional and statistical equivalents to the aforementioned DETERMINANTS. Furthermore, the statistical utility of such additional DETERMINANTS is substantially dependent on the cross-correlation between multiple biomarkers and any new biomarkers will often be required to operate within a panel in order to elaborate the meaning of the underlying biology.

One or more, preferably two or more of the listed DETERMINANTS can be detected in the practice of the present invention. For example, two (2), three (3), four (4), five (5), ten (10), fifteen (15), twenty (20), forty (40), fifty (50), seventy-five (75), one hundred (100), one hundred and twenty five (125), one hundred and fifty (150), one hundred and seventy-five (175), two hundred (200), two hundred and ten (210), two hundred and twenty (220), two hundred and thirty (230), two hundred and forty (240), two hundred and fifty (250), two hundred and sixty (260) or more, two hundred and seventy (270) or more, two hundred and eighty (280) or more, two hundred and ninety (290) or more, DETERMINANTS can be detected.

In some aspects, all 300 DETERMINANTS listed herein (i.e., the KRAS SIGNATURE) can be detected. Preferred ranges from which the number of DETERMINANTS can be detected include ranges bounded by any minimum selected from between one and 300, particularly two, five, ten, twenty, fifty, seventy-five, one hundred, one hundred and twenty five, one hundred and fifty, one hundred and seventy-five, two hundred, two hundred and ten, two hundred and twenty, two hundred and thirty, two hundred and forty, two hundred and fifty, paired with any maximum up to the total known DETERMINANTS, particularly five, ten, twenty, fifty, and seventy-five. Particularly preferred ranges include two to five (2-5), two to ten (2-10), two to fifty (2-50), two to seventy-five (2-75), two to one hundred (2-100), five to ten (5-10), five to twenty (5-20), five to fifty (5-50), five to seventy-five (5-75), five to one hundred (5-100), ten to twenty (10-20), ten to fifty (10-50), ten to seventy-five (10-75), ten to one hundred (10-100), twenty to fifty (20-50), twenty to seventy-five (20-75), twenty to one hundred (20-100), fifty to seventy-five (50-75), fifty to one hundred (50-100), one hundred to one hundred and twenty-five (100-125), one hundred and twenty-five to one hundred and fifty (125-150), one hundred and fifty to one hundred and seventy five (150-175), one hundred and seventy-five to two hundred (175-200), two hundred to two hundred and ten (200-210), two hundred and ten to two hundred and twenty (210-220), two hundred and twenty to two hundred and thirty (220-230), two hundred and thirty to two hundred and forty (230-240), two hundred and forty to two hundred and fifty (240-250), two hundred and fifty to two hundred and sixty (250-260), two hundred and sixty to two hundred and seventy (260-270), two hundred and seventy to two hundred and eighty (270-280), two hundred and eighty to two hundred and ninety (280-290), two hundred and ninety to three hundred and sixty (290-30).

Construction of DETERMINANT Panels

Groupings of DETERMINANTS can be included in "panels." A "panel" within the context of the present invention means a group of biomarkers (whether they are DETERMINANTS, clinical parameters, or traditional laboratory risk factors) that includes more than one DETERMINANT. A panel can also comprise additional biomarkers, e.g., clinical parameters, traditional laboratory risk factors, known to be present or associated with cancer or cancer metastasis, in combination with a selected group of the DETERMINANTS listed in Table 1 and Table 2.

As noted above, many of the individual DETERMINANTS, clinical parameters, and traditional laboratory risk factors listed, when used alone and not as a member of a multi-biomarker panel of DETERMINANTS, have little or no clinical use in reliably distinguishing individual normal subjects, subjects at risk for having a metastatic event, and subjects having cancer from each other in a selected general population, and thus cannot reliably be used alone in classifying any subject between those three states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed.

Despite this individual DETERMINANT performance, and the general performance of formulas combining only the traditional clinical parameters and few traditional laboratory risk factors, the present inventors have noted that certain specific combinations of two or more DETERMINANTS can also be used as multi-biomarker panels comprising combinations of DETERMINANTS that are known to be involved in one or more physiological or biological pathways, and that such information can be combined and made clinically useful through the use of various formulae, including statistical classification algorithms and others, combining and in many cases extending the performance characteristics of the combination beyond that of the individual DETERMINANTS. These specific combinations show an acceptable level of diagnostic accuracy, and, when sufficient information from multiple DETERMINANTS is combined in a trained formula, often reliably achieve a high level of diagnostic accuracy transportable from one population to another.

The general concept of how two less specific or lower performing DETERMINANTS are combined into novel and more useful combinations for the intended indications, is a key aspect of the invention. Multiple biomarkers can often yield better performance than the individual components when proper mathematical and clinical algorithms are used; this is often evident in both sensitivity and specificity, and results in a greater AUC. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

Several statistical and modeling algorithms known in the art can be used to both assist in DETERMINANT selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the DETERMINANTS can be advantageously used. Pathway informed seeding of such statistical classification techniques also may be employed, as may rational approaches based on the selection of individual DETERMINANTS based on their participation across in particular pathways or physiological functions.

Ultimately, formula such as statistical classification algorithms can be directly used to both select DETERMINANTS and to generate and train the optimal formula necessary to combine the results from multiple DETERMINANTS into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of DETERMINANTS used. The position of the individual DETERMINANT on a forward or backwards selected panel can be closely related to its provision of incremental information content for the algorithm, so the order of contribution is highly dependent on the other constituent DETERMINANTS in the panel.

Construction of Clinical Algorithms

Any formula may be used to combine SIGNATURE and DETERMINANT results into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of metastatic disease. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from SIGNATURE and DETERMINANT results in the relevant training population. Amongst other uses, such formula may be intended to map the feature space derived from the SIGNATURE or one or more DETERMINANT inputs to a set of subject classes (e.g. useful in predicting class membership of subjects as normal, at risk for having cancer), to derive an estimation of a probability function of risk using a Bayesian approach (e.g. the risk of cancer or a metastatic event), or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual DETERMINANT measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on Clinical Parameters such as age, gender, race, or sex, where specific formula are used solely on subjects within a class or continuously combining a Clinical Parameter as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al, (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula. An example of this is the presentation of absolute risk, and confidence intervals for that risk, derived using an actual clinical study, chosen with reference to the output of the recurrence score formula in the Oncotype Dx product of Genomic Health, Inc. (Redwood City, Calif.). A further modification is to adjust for smaller sub-populations of the study based on the output of the classifier or risk formula and defined and selected by their Clinical Parameters, such as age or sex.

Combination with Clinical Parameters and Traditional Laboratory Risk Factors

Any of the aforementioned Clinical Parameters may be used in the practice of the invention as DETERMINANT input to a formula or as a pre-selection criteria defining a relevant population to be measured using a particular SIGNATURE, DETERMINANT panel and formula. As noted above, Clinical Parameters may also be useful in the biomarker normalization and pre-processing, or in DETERMINANT selection, panel construction, formula type selection and derivation, and formula result post-processing. A similar approach can be taken with the Traditional Laboratory Risk Factors, as either an input to a formula or as a pre-selection criterion.

Measurement of DETERMINANTS

The actual measurement of levels or amounts of the DETERMINANTS can be determined at the protein or nucleic acid level using any method known in the art. For example, at the nucleic acid level, Northern and Southern hybridization analysis, as well as ribonuclease protection assays using probes which specifically recognize one or more of these sequences can be used to determine gene expression. Alternatively, amounts of DETERMINANTS can be measured using reverse-transcription-based PCR assays (RT-PCR), e.g., using primers specific for the differentially expressed sequence of genes or by branch-chain RNA amplification and detection methods by Panomics, Inc. Amounts of DETERMINANTS can also be determined at the protein level, e.g., by measuring the levels of peptides encoded by the gene products described herein, or subcellular localization or activities thereof using technological platform such as for example AQUA. Such methods are well known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the marker genes according to the activity of each protein analyzed.

The DETERMINANT proteins, polypeptides, mutations, and polymorphisms thereof can be detected in any suitable manner, but is typically detected by contacting a sample from the subject with an antibody which binds the DETERMINANT protein, polypeptide, mutation, or polymorphism and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological fluid as described above, and may be the same sample of biological fluid used to conduct the method described above.

Immunoassays carried out in accordance with the present invention may be homogeneous assays or heterogeneous assays. In a homogeneous assay the immunological reaction usually involves the specific antibody (e.g., anti-DETERMINANT protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}$S $^{125}$I $^{131}$I), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of DETERMINANT proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51).

For DETERMINANT proteins, polypeptides, mutations, and polymorphisms known to have enzymatic activity, the activities can be determined in vitro using enzyme assays known in the art. Such assays include, without limitation, kinase assays, phosphatase assays, and reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

Using sequence information provided by the database entries for the DETERMINANT sequences, expression of the DETERMINANT sequences can be detected (if present) and measured using techniques well known to one of ordinary skill in the art. For example, sequences within the sequence database entries corresponding to DETERMINANT sequences, or within the sequences disclosed herein, can be used to construct probes for detecting DETERMINANT RNA sequences in, e.g., Northern blot hybridization analyses or methods which specifically, and, preferably, quantitatively amplify specific nucleic acid sequences. As another example, the sequences can be used to construct primers for specifically amplifying the DETERMINANT sequences in, e.g., amplification-based detection methods such as reverse-transcription based polymerase chain reaction (RT-PCR). When alterations in gene expression are associated with gene amplification, deletion, polymorphisms, and mutations, sequence comparisons in test and reference populations can be made by comparing relative amounts of the examined DNA sequences in the test and reference cell populations.

Expression of the genes disclosed herein can be measured at the RNA level using any method known in the art. For example, Northern hybridization analysis using probes which specifically recognize one or more of these sequences can be used to determine gene expression. Alternatively, expression can be measured using reverse-transcription-based PCR assays (RT-PCR), e.g., using primers specific for the differentially expressed sequences. RNA can also be quantified using, for example, other target amplification methods (e.g., TMA, SDA, NASBA), or signal amplification methods (e.g., bDNA), and the like.

Alternatively, DETERMINANT protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. (See, WO 04/056456 and WO 04/088309, each of which are hereby incorporated by reference in their entireties) In this regard, other DETERMINANT analytes can be measured using the above-mentioned detection methods, or other methods known to the skilled artisan. For example, circulating calcium ions ($Ca^2$) can be detected in a sample using fluorescent dyes such as the Fluo series, Fura-2A, Rhod-2, among others. Other DETERMINANT metabolites can be similarly detected using reagents that are specifically designed or tailored to detect such metabolites.

Kits

The invention also includes a DETERMINANT-detection reagent, e.g., nucleic acids that specifically identify one or more DETERMINANT nucleic acids by having homologous nucleic acid sequences, such as oligonucleotide sequences, complementary to a portion of the DETERMINANT nucleic acids or antibodies to proteins encoded by the DETERMINANT nucleic acids packaged together in the form of a kit. The oligonucleotides can be fragments of the DETERMINANT genes. For example the oligonucleotides can be 200, 150, 100, 50, 25, 10 or less nucleotides in length. The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or a sandwich ELISA as known in the art.

For example, DETERMINANT detection reagents can be immobilized on a solid matrix such as a porous strip to form at least one DETERMINANT detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of DETERMINANTS present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by DETERMINANTS 1-600. In various embodiments, the expression of 2, 3, 4, 5, 6, 7, 8, 9, 10, 15, 20, 25, 40, 50, 100, 125, 150, 175, 200, 250, 275, 300, 350, 400, 450, 500, 550 or more of the sequences represented by DETERMINANTS 1-600 can be identified by virtue of binding to the array. The substrate array can be on, e.g., a solid substrate, e.g., a "chip" as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.).

Suitable sources for antibodies for the detection of DETERMINANTS include commercially available sources such as, for example, Abazyme, Abnova, Affinity Biologicals, AntibodyShop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, nucleic acid probes, e.g., oligonucleotides, aptamers, siRNAs, antisense oligonucleotides, against any of the DETERMINANTS in Table 1 and Table 2.

TABLE 1

Upregulated Determinants of the KRAS Activation Signature

| Determinant | Determinant No. |
|---|---|
| TNFRSF6B | 1 |
| IL13RA2 | 2 |
| A2M | 3 |
| SCGS | 4 |
| IL1RL1 | 5 |
| ITGA2 | 6 |
| C11ORF41 | 7 |
| FGF9 | 8 |
| G0S2 | 9 |
| CALB1 | 10 |
| HSD11B1 | 11 |
| NRCAM | 12 |
| DOCK4 | 13 |
| SNAP91 | 14 |
| STC1 | 15 |
| TMEM28 | 16 |
| DYNC1I1 | 17 |
| ST3GAL6 | 18 |
| CDR1 | 19 |
| SNAP25 | 20 |
| ANGPTL4 | 21 |
| ETV1 | 22 |
| HNT | 23 |
| MMP11 | 24 |
| GLRX | 25 |
| RBP4 | 26 |
| ITGB2 | 27 |
| ETV5 | 28 |
| PEG3 | 29 |
| RELN | 30 |
| CFHR2 | 31 |
| LMO3 | 32 |
| HEY1 | 33 |
| TERT | 34 |
| LILRA6 | 35 |
| DHRS9 | 36 |
| CD1A | 37 |
| ADAM8 | 38 |
| CD33L3 | 39 |

TABLE 1-continued

Upregulated Determinants of the KRAS Activation Signature

| Determinant | Determinant No. |
|---|---|
| GLDC | 40 |
| KIF5C | 41 |
| PPBP | 42 |
| SCG3 | 43 |
| HPN | 44 |
| PCDH8 | 45 |
| HTR7 | 46 |
| CHGB | 47 |
| GABRA5 | 48 |
| CXCL5 | 49 |
| FABP3 | 50 |
| DMBT1 | 51 |
| CGA | 52 |
| FLJ90013 | 53 |
| SLC25A31 | 54 |
| KCNK10 | 55 |
| RNASE1 | 56 |
| SYT1 | 57 |
| PDE2A | 58 |
| NOL4 | 59 |
| ZNF528 | 60 |
| LOC401034 | 61 |
| NPY6R | 62 |
| FLJ21062 | 63 |
| SMPX | 64 |
| CXCL3 | 65 |
| TFDP3 | 66 |
| EVI2A | 67 |
| KCNK7 | 68 |
| ACCN4 | 69 |
| DNAJA4 | 70 |
| BEX1 | 71 |
| USH1C | 72 |
| ARHGAP24 | 73 |
| EDG2 | 74 |
| GPR4 | 75 |
| ATP1A2 | 76 |
| KIF5A | 77 |
| DUSP6 | 78 |
| RDH5 | 79 |
| DCBLD2 | 80 |
| ADAM19 | 81 |
| ETV4 | 82 |
| CTNNA2 | 83 |
| GBA3 | 84 |
| GRIN2A | 85 |
| LOC653127 | 86 |
| NAV3 | 87 |
| MAPK10 | 88 |
| CHGA | 89 |
| NMES | 90 |
| APOD | 91 |
| ANK3 | 92 |
| RTN1 | 93 |
| SCN1B | 94 |
| CSF3 | 95 |
| SPRY2 | 96 |
| SEMA3A | 97 |
| CEL | 98 |
| MCF2 | 99 |
| TMEM16A | 100 |
| KCNH2 | 101 |
| CEACAM3 | 102 |
| PCP4 | 103 |
| NAP1L2 | 104 |
| ANPEP | 105 |
| MMP1 | 106 |
| FNDC8 | 107 |
| DSCR1L1 | 108 |
| DNM3 | 109 |
| SLC6A15 | 110 |
| C11ORF32 | 111 |
| LOC147343 | 112 |
| DEFB4 | 113 |
| ITGBL1 | 114 |

TABLE 1-continued

Upregulated Determinants of the KRAS Activation Signature

| Determinant | Determinant No. |
|---|---|
| LOC202181 | 115 |
| MAP4K1 | 116 |
| GABRA1 | 117 |
| DDX6 | 118 |
| LRCH1 | 119 |
| CDK5R1 | 120 |
| APOBEC3G | 121 |
| CRISP1 | 122 |
| ERC2 | 123 |
| RRAGD | 124 |
| FLJ23588 | 125 |
| CLUL1 | 126 |
| RETN | 127 |
| GABRA3 | 128 |
| ZP4 | 129 |
| SCN2A2 | 130 |
| TRIB2 | 131 |
| SLCO5A1 | 132 |
| GPR19 | 133 |
| EMID2 | 134 |
| ASTN1 | 135 |
| TNRC9 | 136 |
| DBH | 137 |
| ATXN3L | 138 |
| HIST1H2BO | 139 |
| WNT7A | 140 |
| HAS2 | 141 |
| MKRN3 | 142 |
| TRIM36 | 143 |
| SPP1 | 144 |
| TFPI | 145 |
| OR2B6 | 146 |
| PTX3 | 147 |
| CEACAM1 | 148 |
| LOC339524 | 149 |
| PRG3 | 150 |
| STX1A | 151 |
| CXCR4 | 152 |
| GPR37 | 153 |
| LOC650293 | 154 |
| TAAR5 | 155 |
| TCF8 | 156 |
| GPR124 | 157 |
| MMP9 | 158 |
| CPA2 | 159 |
| IL1F6 | 160 |
| ETV2 | 161 |
| LOC390616 | 162 |
| C10ORF110 | 163 |
| ANP32A | 164 |
| ST18 | 165 |
| KCNJ8 | 166 |
| PRL | 167 |
| ACOX2 | 168 |
| MMP10 | 169 |
| AURKC | 170 |
| VEGFC | 171 |
| TGM2 | 172 |
| TNFSF15 | 173 |
| WNT7B | 174 |
| CSN2 | 175 |
| LOC123876 | 176 |
| TAGLN3 | 177 |
| PCDHA9 | 178 |
| PNMA2 | 179 |
| GFI1 | 180 |
| FEZF2 | 181 |
| PRDM14 | 182 |
| PTGS2 | 183 |
| IL1R2 | 184 |
| KCNAB3 | 185 |
| ZNF529 | 186 |
| DLGAP2 | 187 |
| HBEGF | 188 |
| DNMBP | 189 |
| NTRK3 | 190 |
| PCLKC | 191 |
| CD80 | 192 |
| PIWIL1 | 193 |
| LOC401525 | 194 |
| EMP1 | 195 |
| HS3ST3B1 | 196 |
| KCNK3 | 197 |
| TBX3 | 198 |
| TPH1 | 199 |
| ESM1 | 200 |
| ATP4A | 201 |
| LAPTM5 | 202 |
| CHRNA3 | 203 |
| IFNA8 | 204 |
| IGF2 | 205 |
| KCNC1 | 206 |
| SH2D2A | 207 |
| ZDHHC11 | 208 |
| SPRY4 | 209 |
| DEFA5 | 210 |
| GNG11 | 211 |
| PMS2L4 | 212 |
| TLR8 | 213 |
| CTNND2 | 214 |
| MAGEA11 | 215 |
| ARL4C | 216 |
| LDB3 | 217 |
| SPINK1 | 218 |
| MLXIPL | 219 |
| CEND1 | 220 |
| SLCO4A1 | 221 |
| PLAT | 222 |
| KIT | 223 |
| C14ORF139 | 224 |
| CMKLR1 | 225 |
| MYF6 | 226 |
| DEFA1 | 227 |
| OR2C1 | 228 |
| PFKFB1 | 229 |
| TMEM158 | 230 |
| GALR2 | 231 |
| TRIM2 | 232 |
| PRO0478 | 233 |
| CSF2RA | 234 |
| KRTHB6 | 235 |
| RBMY1A1 | 236 |
| MGC4771 | 237 |
| BMP7 | 238 |
| PLAU | 239 |
| MMD | 240 |
| INHBA | 241 |
| CYP27B1 | 242 |
| GFAP | 243 |
| C13ORF18 | 244 |
| NRP1 | 245 |
| KCNA5 | 246 |
| GRM1 | 247 |
| MTMR8 | 248 |
| SATB1 | 249 |
| MAGEH1 | 250 |
| ITPKA | 251 |
| ALPI | 252 |
| MMP17 | 253 |
| DIRAS2 | 254 |
| SLIT1 | 255 |
| AMBP | 256 |
| LGALS14 | 257 |
| DKFZP686A01247 | 258 |
| MSMB | 259 |
| RP11-35N6.1 | 260 |
| LAG3 | 261 |
| LOC400451 | 262 |
| MOBP | 263 |
| PRG1 | 264 |

TABLE 1-continued

Upregulated Determinants of the KRAS Activation Signature

| Determinant | Determinant No. |
|---|---|
| HIST1H2BB | 265 |
| FLT4 | 266 |
| PELI2 | 267 |
| TEC | 268 |
| MGAT4A | 269 |
| TLR4 | 270 |
| TRIM45 | 271 |
| KCNJ13 | 272 |
| PCDH9 | 273 |
| C10ORF81 | 274 |
| GPR18 | 275 |
| DUSP4 | 276 |
| PLA2G4C | 277 |
| TMEM156 | 278 |
| LOC651803 | 279 |
| EN2 | 280 |
| IGKC | 281 |
| TSPY1 | 282 |
| KRT8L2 | 283 |
| SOX9 | 284 |
| PLA2G3 | 285 |
| SEC15L2 | 286 |
| CCNJL | 287 |
| C1QTNF1 | 288 |
| NMNAT2 | 289 |
| CCR6 | 290 |
| REEP2 | 291 |
| FMNL2 | 292 |
| FLJ13310 | 293 |
| ALDH8A1 | 294 |
| LPXN | 295 |
| ADCYAP1R1 | 296 |
| EDG2 | 297 |
| UGT8 | 298 |
| CLSTN2 | 299 |
| FOXG1B | 300 |

TABLE 2

Downregulated Determinants of the KRAS Activation Signature

| Determinant | Determinant No. |
|---|---|
| KRT13 | 301 |
| S100A7 | 302 |
| KRT4 | 303 |
| KRT16 | 304 |
| TGM1 | 305 |
| CDH16 | 306 |
| CXCR7 | 307 |
| NOS1 | 308 |
| EPHX2 | 309 |
| IFI44L | 310 |
| KRT38 | 311 |
| IGF2AS | 312 |
| LY6D | 313 |
| SPRR1B | 314 |
| SLC6A14 | 315 |
| KIF25 | 316 |
| SERPINB13 | 317 |
| SPRR3 | 318 |
| DXS542 | 319 |
| MX2 | 320 |
| GPR77 | 321 |
| THRB | 322 |
| RRAD | 323 |
| SOX11 | 324 |
| PTPRCAP | 325 |
| PYHIN1 | 326 |
| PPFIA3 | 327 |
| NTF3 | 328 |

TABLE 2-continued

Downregulated Determinants of the KRAS Activation Signature

| Determinant | Determinant No. |
|---|---|
| HTR1B | 329 |
| LOC440895 | 330 |
| TRPM2 | 331 |
| SLC6A3 | 332 |
| ATP6V1B1 | 333 |
| TUBAL3 | 334 |
| SDS | 335 |
| ABCB1 | 336 |
| C1R | 337 |
| PCDHB1 | 338 |
| FLJ22662 | 339 |
| EPHB6 | 340 |
| CRYGD | 341 |
| TAS2R4 | 342 |
| OLFML2A | 343 |
| HYAL4 | 344 |
| CCR8 | 345 |
| CGREF1 | 346 |
| SCGB1A1 | 347 |
| PSORS1C1 | 348 |
| GADD45G | 349 |
| NCR3 | 350 |
| GRM2 | 351 |
| HAAO | 352 |
| DFNB31 | 353 |
| NR0B2 | 354 |
| AKR1B10 | 355 |
| TNFSF10 | 356 |
| CLDN16 | 357 |
| DTNB | 358 |
| MYL9 | 359 |
| BRDT | 360 |
| UGT2B17 | 361 |
| CAMK1D | 362 |
| TTLL1 | 363 |
| TREM2 | 364 |
| LFNG | 365 |
| PLEKHH3 | 366 |
| FLJ21687 | 367 |
| CACNA1I | 368 |
| HTR1D | 369 |
| NPC1L1 | 370 |
| CBL | 371 |
| CSDC2 | 372 |
| DKFZP434O047 | 373 |
| COBL | 374 |
| PDE6B | 375 |
| GBP1 | 376 |
| IFNA17 | 377 |
| RPIB9 | 378 |
| KRT1 | 379 |
| CTSW | 380 |
| C9ORF127 | 381 |
| CIITA | 382 |
| EDAR | 383 |
| LGALS7 | 384 |
| BST2 | 385 |
| RASAL1 | 386 |
| FGFR3 | 387 |
| DPYS | 388 |
| SIDT1 | 389 |
| GKN1 | 390 |
| CRABP2 | 391 |
| MAP2K6 | 392 |
| DPT | 393 |
| SLC30A4 | 394 |
| DSG3 | 395 |
| KCNMB2 | 396 |
| KIAA1660 | 397 |
| MXD3 | 398 |
| CHRM2 | 399 |
| CA5B | 400 |
| SYNPO | 401 |
| DTX2 | 402 |
| PROC | 403 |

TABLE 2-continued

Downregulated Determinants of the KRAS Activation Signature

| Determinant | Determinant No. |
|---|---|
| TNNI3 | 404 |
| NKX6-1 | 405 |
| KCNE1 | 406 |
| SLC3A1 | 407 |
| CYP2A6 | 408 |
| APOB | 409 |
| IGKV1D-13 | 410 |
| EDIL3 | 411 |
| LOC92154 | 412 |
| VILL | 413 |
| MAML3 | 414 |
| POM121L2 | 415 |
| MXRA8 | 416 |
| AMBN | 417 |
| GOLGA | 418 |
| TAGLN | 419 |
| TM4SF4 | 420 |
| LOC390998 | 421 |
| IGHA1 | 422 |
| PODNL1 | 423 |
| YBX2 | 424 |
| COLEC10 | 425 |
| ACTG2 | 426 |
| PROP1 | 427 |
| H2AFB3 | 428 |
| ZNF750 | 429 |
| DENND1C | 430 |
| APBB3 | 431 |
| RYR2 | 432 |
| TEX15 | 433 |
| P2RX1 | 434 |
| CEACAM5 | 435 |
| SLC9A7 | 436 |
| SPTBN2 | 437 |
| FOXI1 | 438 |
| OAS1 | 439 |
| RTP4 | 440 |
| MX1 | 441 |
| PDE11A | 442 |
| PCYT1B | 443 |
| TNFRSF13B | 444 |
| CD40LG | 445 |
| FMO6 | 446 |
| HOXB8 | 447 |
| KCNQ3 | 448 |
| HSPB8 | 449 |
| MUC5AC | 450 |
| PRTN3 | 451 |
| ABCG4 | 452 |
| CYP2C18 | 453 |
| SCRT1 | 454 |
| KRT31 | 455 |
| IFNA5 | 456 |
| HIST1H3A | 457 |
| IFNA16 | 458 |
| KLK7 | 459 |
| CKM | 460 |
| FLJ10986 | 461 |
| AQP6 | 462 |
| TRH | 463 |
| SPRR1A | 464 |
| OPN1MW | 465 |
| HLA-DOA | 466 |
| UGT2A3 | 467 |
| CNTFR | 468 |
| KRT17 | 469 |
| FCGBP | 470 |
| LOC650620 | 471 |
| CXCL14 | 472 |
| CLDN8 | 473 |
| ARHGAP28 | 474 |
| SCGN | 475 |
| LSP1 | 476 |
| CYP2C19 | 477 |
| C22ORF31 | 478 |
| DLX6 | 479 |
| IL19 | 480 |
| DSG1 | 481 |
| BIRC4BP | 482 |
| BLNK | 483 |
| IGSF4C | 484 |
| BCL11B | 485 |
| GPR173 | 486 |
| EDN2 | 487 |
| SIT1 | 488 |
| CLIC3 | 489 |
| C8ORF59 | 490 |
| PCDHGB6 | 491 |
| GNRH2 | 492 |
| CCDC33 | 493 |
| MAPRE3 | 494 |
| FLJ11827 | 495 |
| SLAMF1 | 496 |
| TGFB2 | 497 |
| DDX51 | 498 |
| NEU3 | 499 |
| CD36 | 500 |
| FGF4 | 501 |
| MYOM2 | 502 |
| LGALS9 | 503 |
| ADRA2B | 504 |
| CSPG4 | 505 |
| BBC3 | 506 |
| NRXN3 | 507 |
| SERPING1 | 508 |
| HOXC8 | 509 |
| ZBP1 | 510 |
| C8A | 511 |
| PTPRH | 512 |
| LRRC31 | 513 |
| KCNMB1 | 514 |
| KLF8 | 515 |
| PRRG4 | 516 |
| RP5-1119A7.4 | 517 |
| IGLV2-14 | 518 |
| LOC644872 | 519 |
| LOC57399 | 520 |
| COL2A1 | 521 |
| PIP5K1C | 522 |
| FLJ20712 | 523 |
| EDN1 | 524 |
| HRASLS | 525 |
| HRH3 | 526 |
| FLJ10916 | 527 |
| CALML5 | 528 |
| ZBTB16 | 529 |
| EPHB3 | 530 |
| CD300A | 531 |
| IL5 | 532 |
| KLK12 | 533 |
| FRAS1 | 534 |
| SCN7A | 535 |
| THBD | 536 |
| KIAA0087 | 537 |
| SCN10A | 538 |
| YOD1 | 539 |
| WNT16 | 540 |
| PRODH | 541 |
| LYPD3 | 542 |
| NINJ1 | 543 |
| GP2 | 544 |
| PIK3C2B | 545 |
| CNGB1 | 546 |
| C1QL1 | 547 |
| 2-Apr | 548 |
| CTAG2 | 549 |
| SPATA6 | 550 |
| SLC22A11 | 551 |
| MLANA | 552 |
| SPAG11 | 553 |

TABLE 2-continued

Downregulated Determinants of the KRAS Activation Signature

| Determinant | Determinant No. |
|---|---|
| CHRNG | 554 |
| KLF3 | 555 |
| ADAMTS9 | 556 |
| PGLYRP1 | 557 |
| VGLL3 | 558 |
| LOC441259 | 559 |
| TRIM48 | 560 |
| VAV3 | 561 |
| ZNF154 | 562 |
| CALML3 | 563 |
| NAALADL1 | 564 |
| CXORF48 | 565 |
| SMPDL3B | 566 |
| NOX3 | 567 |
| MCHR1 | 568 |
| CCDC102B | 569 |
| PNMT | 570 |
| FLJ20184 | 571 |
| NR1I3 | 572 |
| ABCB11 | 573 |
| KIAA1305 | 574 |
| ART1 | 575 |
| CLCA2 | 576 |
| ANKRD1 | 577 |
| CALCB | 578 |
| SLC5A2 | 579 |
| IMPA2 | 580 |
| ENPP1 | 581 |
| RAMP3 | 582 |
| CD207 | 583 |
| C14ORF161 | 584 |
| CD248 | 585 |
| GPR52 | 586 |
| FETUB | 587 |
| CNR2 | 588 |
| MATN2 | 589 |
| MAST3 | 590 |
| APOL3 | 591 |
| SLC29A3 | 592 |
| DBF4B | 593 |
| CST4 | 594 |
| ATP2A3 | 595 |
| MTNR1A | 596 |
| PTPRU | 597 |
| EGFL9 | 598 |
| FOLR2 | 599 |
| IVL | 600 |

EXAMPLES

Example 1

Identification of a KRAS Activation Signature

Signatures of oncogenic KRAS activation were generated from the expression profiling of immortalized human epithelial cells (Breast, Prostate, Kidney and Lung) each transduced either with an activated allele of KRAS or a control vector. Each experiment was performed in duplicate. The samples were profiled using Affymetrix U133 arrays and the signatures defined by the top/bottom 100 and 300 differentially expressed genes, according to their mean difference, between the "activated" vs. "control" classes for the 4 cell lineages. An analysis of the genes revealed not just a proliferation signature but rather a complex collection of diverse biological processes. We used these signatures to build a simple scoring model using a single-sample Gene Set Enrichment Analysis (GSEA) method as described in Barbie et al. 2009.

Briefly, first we mapped probe ids to gene symbols, rank normalized each sample, and then for each of the KRAS signatures we defined a score representing the degree of absolute enrichment per sample. The score is produced by evaluating an "enrichment" statistic that is a function of the differences in the Empirical Cumulative Distribution Functions (ECDF) of the genes in the gene set vs. the rest. This procedure is similar to the one used in Gene Set Enrichment Analysis (GSEA) but instead of using a gene list ranked by differential expression, the list is ranked by absolute expression (in one sample), and the enrichment score is obtained, not by a weighted Kolmogorov-Smirnov statistic like in GSEA, but by an integration of the difference between the ECDFs.

In addition to "UP" and "DN" scores corresponding to the up-regulated (UP) and down-regulated (DN) portions of the signature, a combined score is computed from both scores. We applied this procedure using a consensus signature derived from all the lineages to the same samples in the training dataset and confirmed that the activation score in all the lineages is higher in the KRAS activated samples and lower in the controls as expected. The fact that the activation score is high in all the mutant KRAS samples regardless of lineage indicates that the signature is able to represent activation across 4 lineages (lung, breast, prostate and kidney).

Figure 2:
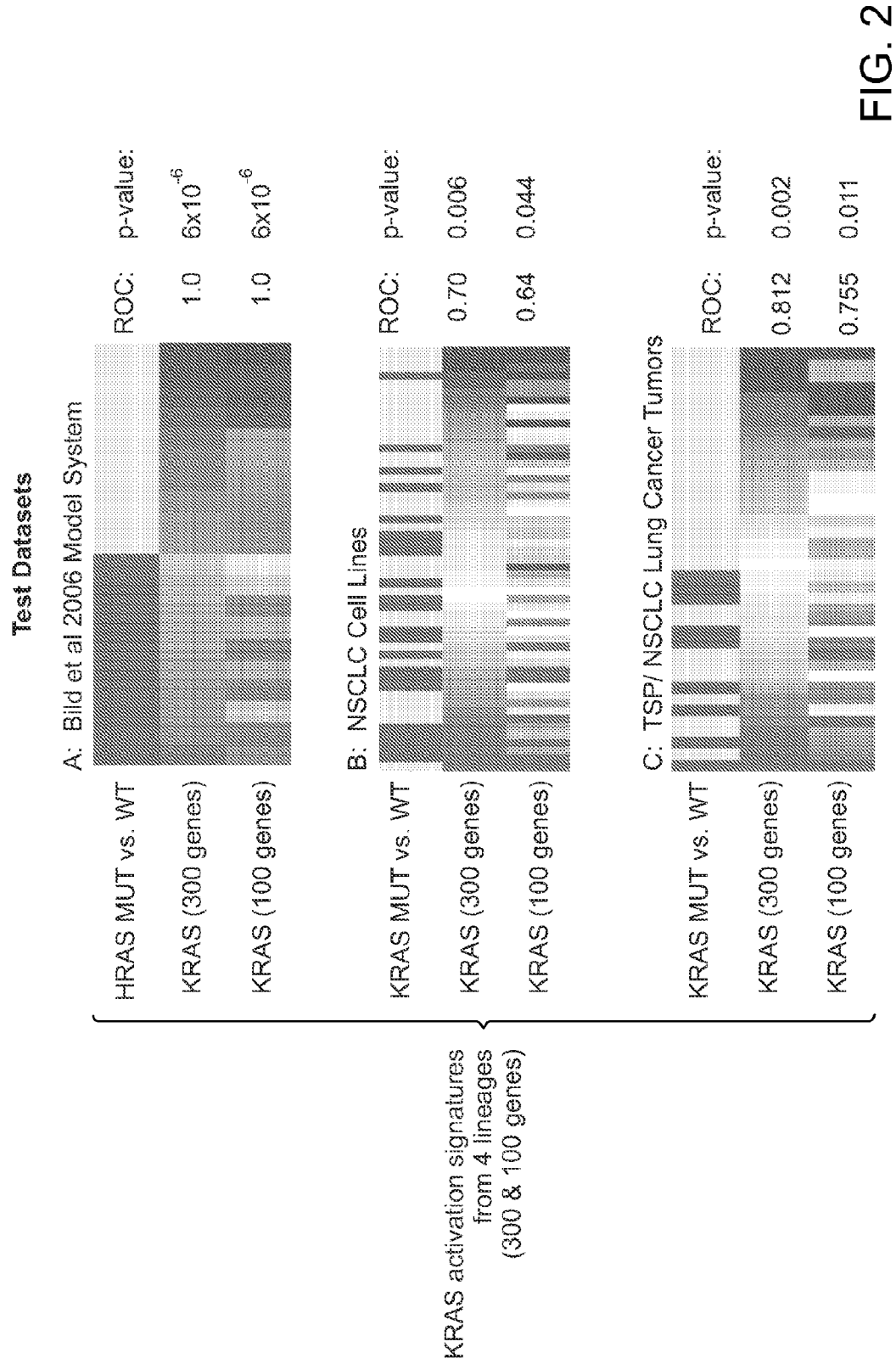
FIG. 2 is an illustration showing oncogenic KRAS Activation Signature Models. The samples have been sorted according to the activation score of the KRAS gene signatures. The top black and grey bars denote the phenotype (MUT. vs. WT respectively). The numbers of the left side are the area under the Receiver Operating Characteristic (ROC) for each signature as a predictor of phenotype and associated p-value.

We applied these signatures and scoring models to other cell-based experimental models where the activation status of KRAS is known (FIG. 2) such as the dataset of Bild et al. 2006. In this dataset, breast epithelial cells were activated by retroviral infection of mutant HRAS. We found excellent concordance (area under ROC: 1.0, p-value: $6 \times 10^{-6}$) as can be seen in FIG. 2A, where the samples have been sorted according to decreasing activation score of the KRAS gene signature. The top bar shows the phenotype of the samples, in this case cells transduced with mutant HRAS, in dark gray vs. controls in light gray. The KRAS 100-gene activation profiles are also shown for comparison. On the left side of the plot the areas under the ROC for predicting the phenotype and associated p-value are shown. Next we scored a group of 53 non-small cell lung cancer (NSCLN) adenocarcinoma cell lines from the Meyerson Lab and obtained a significant segregation of the cell lines with mutant KRAS/HRAS (area under ROC: 0.7, p-value: 0.006). Finally we scored a collection of 38 NSCLN adenocarcinoma lung tumors from the Tumor Sequencing Project [30]. Here the models also worked well at segregating tumors with KRAS mutations: area under ROC: 0.812 and p-value: 0.002).

These preliminary results show that a common signature of KRAS activation can be used to identify samples in both cell lines and human tumors with mutant versions of the relevant oncogene. Our preliminary results suggest that our first generation experimentally-derived KRAS signature has reasonable predictive power.

Example 2

Creating a Statistical Scoring Models Based on the Oncogenic Signatures

Many aspects of the statistical methodology required for creating a model based upon the KRAS signature can be addressed casting the overall problem as one of statistical inference and supervised learning (e.g., train the statistical model on training data from the cell model system, and then score test samples using that trained model). However, as the target test datasets will consist of tumors that incorporate significant in vivo differences with respect to the training in vitro model systems, the setting is not one of straightforward classification where the probability distributions of train and test samples are identical.

As described below, in the last few years we have developed a methodology for single-sample Gene Set Enrichment Analysis (ssGSEA). Given a gene set, this method is able to provide numerical scores corresponding to the amount of enrichment or activation of the gene set in a single test sample. We will use this method as the starting point of our methodological development. For example, the current method only generates signatures using a given gene's dataset but we will have to use multiple datasets corresponding to several genes so that their pathway-specificity and sensitivity can be improved. This one-vs.-all approach would be useful to eliminate common transcriptional programs, such as increase in proliferation, that could dominate a single-oncogene signature but do not provide a specific enough signal. Another limitation of the current methodology is its limited pre-normalization procedure and the fact that genes with low expression contribute less to enrichment scores than genes with high expression. This can be improved using prior information from, e.g., a large compendium of gene-expression data such as the Gene Expression Omnibus (GEO). In this way each gene or gene set can be rescaled according to its behavior as observed in thousands of samples and not only in the training dataset.

These improvements can be better conceptualized and implemented if we adopt a Bayesian viewpoint. We will develop our methodology as a problem of Bayesian inference/regression using state-of-the-art mixture modeling and Monte Carlo/Gibbs sampling. The proposed modeling will require a significant effort on the computational and statistical side but it will provide an extremely powerful paradigm and tool to perform signature-based scoring. An additional benefit of a Bayesian approach is that it facilitates using prior information in a principled way and also that it provides an information-rich posterior distribution of the model parameters rather than point estimates. This is the way we envision the new proposed methodology:

1. Pre-Processing and Normalization.

We will normalize each training and validation dataset prior to training or testing procedures in order to put each gene-expression value on a comparable scale across train and test samples. We have used a rank normalization approach in the past but we will extend that by creating individual component mixture models fit on a large group of samples from compendia such as the Gene Expression Omnibus (GEO). We will use this model to rescale each gene value to its "true" normalized value based on its behavior in those GEO samples. This last approach is challenging but it is worthwhile to consider given the large amount of existing gene expression data and the potential benefit in terms of better normalization overall.

2. Signature Generation.

In our current methodology, we select genes by the difference in class means, or by the signal to noise ratio, across activation and control phenotypes (see Preliminary Results). For the new methodology we will create UP and DOWN versions of the signatures by selecting normalized genes according to Bayesian measures of discrimination such as Bayes factors or the specific amount of "evidence" (average absolute posterior log odds ratio[37]) they convey about the class phenotype (i.e., c=Active or c=Control). For example, for the UP (Active) signature of KRAS the evidence that a gene x provides regarding the (mutant) status of KRAS is:

$$E_{KRAS}(x, c = \text{Active}) = \sum_i^N \left| \log \frac{P(c = \text{Active}|x_i)/P(c = \text{Control}|x_i)}{P(c = \text{Active})/P(c = \text{Control})} \right|,$$

where the $x_i$ are gene expression values in each of N samples for gene x. The conditional probabilities in that expression can be estimated by either: i) discretization of the gene expression values, or ii) by fitting a continuous model such as Bayesian logistic regression. A threshold $E^*$ on the amount of evidence, either according to a specific False Discovery Rates (FDR) or other criteria, can be used to define the size of the signature $$S_{KRAS}^{UP} = \{x | E_{KRAS}(x, c=\text{Active}) \geq E^*\},$$

in such way that it contains only the top G most informative genes. For each gene we will generate individual signatures for each lineage and multiple-lineage versions.

3. Creating (Training) Scoring Models.

Once a signature has been generated it can be used to produce a model to score test samples and evaluate the degree of oncogene activation or tumor suppressor deregulation. Typically the scoring model reduces the normalized gene expression for the genes in a given signature to a single numerical value. In the existing methodology (see Preliminary Results) we use the difference between the empirical distribution functions of genes in the signature vs. the rest as a measure of activation. In the new methodology we will use a Bayesian linear regression model to generate "weights" for each gene. We will accomplish this by fitting a linear model to the training dataset under the assumption that the signature score can be summarized with one, or more, latent variables that become the numerical representative of the signature. The more consistently the genes in the signature behave across samples in the training set the more they contribute to the score. This can be expressed more formally as, $S_{G \times N}^{UP} = W_{G \times k}^{UP} \times L_{k \times N}^{UP}$, where $S_{G \times N}^{UP}$ is an "UP" expression signature matrix for a given oncogene with G genes (selected as described above) in N samples. The matrix $W_{G \times k}^{UP}$ represents a set of weights corresponding to each gene in each of k latent variables. The matrix $L_{k \times N}^{UP}$ contains the latent variables that represent the coherent behaviors of the signature across the N training samples. Notice that in the decomposition both the weight matrix $W_{G \times k}^{UP}$ and the latent variable matrix $L_{k \times N}^{UP}$ are unknown and the Bayesian decomposition determines their posterior probability distributions as instances of a Markov Chain Monte Carlo process. They have to be estimated so that the product approximates the known, observed signature matrix $S_{G \times N}^{UP}$. The specific value of k for a given training dataset will be determined by Bayesian model selection. If the signature behaves coherently in the training set, then it will be represented by just one latent variable (k=1) with the matrix $W_{G \times k}^{UP}$ becoming a weighting vector. If the signature contains more than one latent variable, then it will have multiple scores, one for each latent variable. In order to convert these signature scores into a final single probability score we will build a second Bayesian model (e.g., using logistic regression) using combinations of the latent variables as inputs and then fitting the model to the activation/deregulation phenotype.

The latent variable regression model is similar to our metagene projection methodology based on non-negative matrix factorization (NMF). The main difference is that here the model is fit using only the signature's genes rather than all of the genes, and the fit is achieved by Monte Carlo sampling (in a Bayesian context) rather than using NMF iterations. To make the method very general and flexible we will adopt a sampling strategy similar to the one recently introduced by Mikkel Schmidt. This has the advantage of supporting a wide range of constraints with NMF being a special case. The importance of this approach derives from the extra flexibility it gives when the right structure of the weight and latent variable matrices is unknown. We plan to adapt it for the specific purposes of our scoring model. For this part of the methodology we will also experiment with other Bayesian decomposition approaches.

We are separating the signature generation from the training of scoring models in order to have the signatures defined by gene membership rather than depending on the scoring model. In this way, other signature-based approaches developed by the community (e.g., GSEA) might also use these gene sets as inputs.

4. Signature Validation.

Once the latent variables and associated logistic regression models are trained, one can score (predict) a new test sample $s_t$ by projecting it into the space of the latent variables, e.g., using the matrix pseudo-inverse of $W_{G \times k}^{UP}$ and $W_{G \times k}^{UP}$, and then using the logistic model to produce a final probability score. The validation of the model will involve projecting an entire dataset of independent test samples and determining how well the model predicts their known gene activation/deregulation status.

5. Signature Refinement.

For some signatures a process of "refinement" may be necessary to make the signatures work in both the "acute" activation space of the training dataset and also in the steady state "chronic" activation state in the tumor in vivo environment. One simple approach to signature refinement would be to trim the signatures to a narrower transcriptional subspace that is common between the training and tumor test datasets. An advantage of the latent variable approach described above is that it automatically provides us with a method for signature refinement. For example, we could add a group of test datasets to the training data and then select the value of k to be optimal in terms of reproducing the extended signature matrix. Under this approach the signature weights will reflect not only how consistent the genes are in the training data, but also how consistently they behave in additional test samples. This could help de-emphasize parts of the signature that do not behave consistently in the in vivo context. After refinement, a final validation will be performed on an independent collection of test sets. We will describe the validation datasets in more detail in the next section.

As this proposed methodology implies a considerable amount of computational and statistical work, we are allocating a full time computational biologist (Aviad Tsherniak) with prior experience with this kind of data and approach. This is also the reason the Principal Investigator will dedicate 50% effort to the project.

Example 3

Validation of the Signature Models and Assessment of their Universality and Tissue Specificity As the validation process is a critical component of we will validate the signatures and models in several cell line and tumor collections:

The Broad-Novartis Cell Line Encyclopedia (CLE) is collaboration between the Broad Institute, the Novartis Institutes for Biomedical Research and the Genomics Novartis Foundation. It will contain comprehensive genomic profiling and annotation for 1,000 cell lines (Garraway support letter).

COSMIC is a public repository at the Welcome Trust Sanger Institute containing somatic mutations, samples and other information relating to human cancers.

The Cancer Genome Atlas (TCGA) and the Tumor Sequencing Project are NIH/NCI sponsored efforts, in which the Broad Institute participates, to catalogue cancer genetic mutations by large-scale sequencing. We will use the GBM, Ovarian, Squamous Lung and other datasets from those efforts (Meyerson and Getz support letters).

Tumor Datasets from Collaborators and the Literature.

The validation of the signatures in the CLE will give the first indication of how well they generalize to new instances that are more complex than the original training model systems, but more homogeneous than human tumors. This validation set will also allow us to determine how various experimental and computational manipulations affect the sensitivity and specificity of the signatures, investigate instances of errors, and generate hypotheses about their cause.

Signatures that validate on cell line data, will next be tested on expression data from human tumors that harbor the relevant mutations in an in vivo context. These datasets will allow us to determine whether our method is sensitive enough to detect specific oncogene or tumor suppressor activation or deregulation in a tumor context, and to assess the universality or lineage specificity of each signature model. For example, to validate the signature of KRAS activation we will use tumor datasets where the mutational status of KRAS has been determined, such as an NSCLC dataset from the Meyerson laboratory. A subset of the validation datasets may be used for refinement purposes if necessary. One advantage of using multiple cell lines is that they harbor the same genetic lesions with very different backgrounds and may allow for a more universal and realistic refinement process. Data used for refinement will not be used for subsequent validation.

We claim:
1. A method comprising:
   a. assaying a biological sample from a subject to determine whether the subject has a tumor or is at risk of developing a tumor, by detecting expression of at least two determinants selected from a KRAS activation profile, wherein the determinants are ITGB2 and HEY1;
   b. comparing the expression of said determinants to the expression of said determinants in a reference sample known to be free of tumor(s);
   c. determining that the subject has a tumor or is at risk of developing a tumor if the determinants are upregulated in comparison to the reference sample; and
   d. administering a treatment regimen, comprising administration of a prophylactic or a therapeutic compound that targets the KRAS oncogene or RAS pathway if the subject is determined to have a tumor.

2. The method of claim 1, further comprising detecting the expression level of one or more markers selected from the group consisting of Determinants 1-26, 28-32, and 34-600 listed in Tables 1 and 2.

3. The method of claim 1, further comprising measuring at least one standard parameter associated with a tumor.

4. The method of claim 1, wherein the biological sample is taken from the subject prior to being treated for a tumor.

5. The method of claim 1, wherein the biological sample is taken from the subject after being treated for a tumor.

* * * * *